United States Patent
Duggan et al.

(10) Patent No.: US 9,624,189 B2
(45) Date of Patent: Apr. 18, 2017

(54) FLUORINATED BENZOFURAN DERIVATIVES

(71) Applicant: SciFluor Life Sciences, Inc., Cambridge, MA (US)

(72) Inventors: Mark E. Duggan, Wellesley, MA (US); Takeru Furuya, Cambridge, MA (US); D. Scott Edwards, Bedford, MA (US)

(73) Assignee: SciFluor Life Sciences, Inc., Cambridge, MA (US)

( * ) Notice: Subject to any disclaimer, the term of this patent is extended or adjusted under 35 U.S.C. 154(b) by 825 days.

(21) Appl. No.: 13/796,248

(22) Filed: Mar. 12, 2013

(65) Prior Publication Data

US 2013/0274325 A1    Oct. 17, 2013

Related U.S. Application Data

(60) Provisional application No. 61/625,359, filed on Apr. 17, 2012, provisional application No. 61/698,994, filed on Sep. 10, 2012.

(51) Int. Cl.
*A61K 31/34* (2006.01)
*C07D 307/80* (2006.01)

(52) U.S. Cl.
CPC .................................. *C07D 307/80* (2013.01)

(58) Field of Classification Search
CPC .............................. C07D 307/80; A61K 31/34
USPC .......................................... 514/469; 549/468
See application file for complete search history.

(56) References Cited

U.S. PATENT DOCUMENTS

| 4,575,513 | A  | * | 3/1986 | Descamps | ............ | C07D 307/80 |
|           |    |   |        |          |              | 514/469 |
| 5,118,707 | A  | * | 6/1992 | Chatterjee | ............ | A61K 31/34 |
|           |    |   |        |          |              | 514/469 |
| 6,221,335 | B1 | * | 4/2001 | Foster   | ................ | C07B 59/002 |
|           |    |   |        |          |              | 424/1.81 |

OTHER PUBLICATIONS

Nagib et al (Nature, 2011,224-228).*
Kozlik et al (Xenobiotica, 2001, 31(5), 239-248).*
Thayer (Chemical & Engineering News, 2006, 84(23), 15-24).*
Conrad, J.: "SciFluor Life Sciences Debuts with Late-Stage Fluorination Technology, Discovered at Harvard University, to Improve Drug Properties for the Pharmaceutical and Biotechnology Industries", May 17, 2011. Retrieved from the Internet on Apr. 15, 2013: URL:http://www.businesswire.comjnewsjhome/20110517005391/enjSciFluor-Life-Sciences-Debuts-Late-Stage-Fluorination-Technology.
Müller, K. et al., "Fluorine in pharmaceuticals: looking beyond intuition", *Science*, 317:1881-1886 (2007).
Trybulski, E.J., "Anti-arrhythmic agents", *Expert Opinion on Therapeutic Patents*, 7(5):457-469 (1997).
"Bruxelles Medical", No. 9, Sep. 1969, pp. 543-560.

* cited by examiner

*Primary Examiner* — Jason Sims
*Assistant Examiner* — Ibrahim D Bori
(74) *Attorney, Agent, or Firm* — Cooley LLP; Ivor R. Elrifi; Heidi A. Erlacher

(57) ABSTRACT

The invention relates to fluorinated compounds and their use in the field of pathological syndromes of the cardiovascular system. Novel fluorinated benzofuran derivatives of amiodarone and pharmaceutically acceptable salts or solvates thereof and their use for the treatment of arrhythmias are described.

16 Claims, No Drawings

FLUORINATED BENZOFURAN DERIVATIVES

RELATED APPLICATIONS

This application claims priority under 35 U.S.C. §119(e) to U.S. provisional application Nos. 61/625,359 and 61/698,994, respectively filed on Apr. 17, 2012 and Sep. 10, 2012, which are incorporated herein by reference.

BACKGROUND

Two major types of arrhythmias are tachycardias (the heartbeat is too fast—more than 100 beats per minute), and bradycardia (the heartbeat is too slow—less than 60 beats per minute). Arrhythmias can be life-threatening if they cause a severe decrease in the pumping function of the heart. When the pumping function is severely decreased for more than a few seconds, blood circulation is essentially stopped, and organ damage (such as brain damage) may occur within a few minutes. Life threatening arrhythmias include ventricular tachycardia and ventricular fibrillation. Amiodarone or 2-n-butyl 3-[4-(2-diethylaminoethoxy) 3,5-diiodo benzoyl]benzofuran has been approved in an oral tablet form (CORDARONE®) for the treatment of life-threatening ventricular tachyarrhythmias in the United States. This drug is useful not only in treating these arrhythmias but also in treating less severe ventricular arrhythmias and many superventricular arrhythmias including atrial fibrillation and reentrant tachyarrhythmias involving accessory pathways.

Despite the beneficial activities of amiodarone, it is practically insoluble or slightly soluble in an aqueous solvent. Hence, it is difficult to formulate a dosage form suitable for administration. Furthermore, amiodarone has unwanted side effects. For example, treatment can result in hypothyroidism. Amiodarone and its des-ethyl metabolite display an undesirable prolonged residence time in tissues. Amiodarone causes phospholipidosis in the lung, which results in the destruction of macrophages in the alveoli. This destruction is expressed in the patient undergoing treatment with amiodarone by the appearance of pulmonary complications, such as respiratory insufficiency, which require the cessation of treatment. Thus, there is a continuing need for new compounds to treat or prevent arrhythmias and other pathological syndromes of the cardiovascular system.

DETAILED DESCRIPTION OF THE INVENTION

For purposes of the present invention, the following definitions will be used (unless expressly stated otherwise):

The term "a compound of the invention" or "compounds of the invention" refers to a compound(s) disclosed herein e.g., a compound(s) of the invention includes a compound(s) of any of the formulae described herein including formulae I, II, III, IV, V, VI, VII, VIII, or IX and/or a compound(s) explicitly disclosed herein. Whenever the term is used in the context of the present invention it is to be understood that the reference is being made to the free base and deuterium labeled compounds, and the corresponding pharmaceutically acceptable salts or solvates thereof, provided that such is possible and/or appropriate under the circumstances.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient(s) and salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

Some of the compounds of the present invention may exist in unsolvated as well as solvated forms such as, for example, hydrates.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the invention.

The invention also includes metabolites of the compounds described herein.

Physiologically acceptable, i.e. pharmaceutically compatible, salts can be salts of the compounds of the invention with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine.

When any variable (e.g., X) occurs more than one time in any constituent or formula for a compound, its definition at each occurrence is independent of its definition at every other occurrence. Thus, for example, if a group is shown to be substituted with one or more X moieties, then X at each occurrence is selected independently from the definition of X. Also, combinations of substituents and/or variables are permissible, but only if such combinations result in stable compounds within a designated atom's normal valency.

As used herein, the term "treat," "treating," or "treatment" herein, is meant decreasing the symptoms, markers, and/or any negative effects of a condition in any appreciable degree in a patient who currently has the condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one aspect, the subject is a human. In one aspect, the subject is a male. In one aspect, the subject is a female.

As used herein, the term a "fluorinated derivative" is a derivative compound that has the same chemical structure as the original compound, except that at least one atom is replaced with a fluorine atom or with a group of atoms containing at least one fluorine atom.

The problem to be solved by the present invention is the identification of novel compounds for the treatment and/or prevention of arrhythmias and related disorders. Although drugs for arrhythmias and related disorders are available, these drugs are often not suitable for many patients for a variety of reasons. For example, many of the available arrhythmia drugs have an inconvenient or ineffective mode of administration. Many arrhythmia drugs are associated with adverse effects. For example, adverse side effects may include hypothyroidism, toxic effect on brain or spinal cord function, abnormally low blood pressure, interstitial pneumonitis, lung fibrosis, inflammation of the alveoli of the lungs, sun-sensitive skin, and abnormal liver function tests. Further, some arrhythmia drugs display an undesirable prolonged residence time in tissues. The present invention provides the solution of new fluorinated benzofuran derivatives for the treatment and/or prevention of arrhythmias and related disorders. The fluorinated compounds described herein have the advantage of providing improved potency, selectivity, tissue penetration, half-life, and/or metabolic stability.

Compounds of the Invention

The present invention relates to novel fluorinated benzofuran derivatives and their use. The present invention relates the synthesis of fluorinated benzofuran derivatives.

In one aspect, the invention provides a compound of formula I:

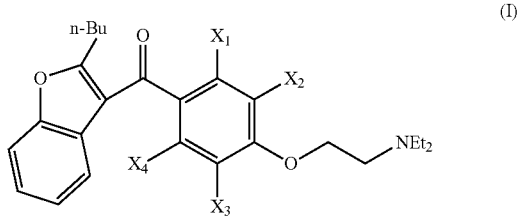

(I)

or a pharmaceutically acceptable salt or solvate thereof, wherein $X_1$, $X_2$, $X_3$, and $X_4$ are each independently selected from hydrogen, I, F, $CF_3$, $CHF_2$, $CH_2F$, $OCF_3$, $OCHF_2$, and $OCH_2F$, provided that when $X_1$ and $X_4$ are each a hydrogen, then $X_2$ and $X_3$ are not both iodine. In one aspect, the invention provides a compound of formula I, provided that the compound has at least one fluorine atom or has a group of atoms containing at least one fluorine atom. In one aspect, the invention provides a compound of formula I, provided that at least one of $X_1$, $X_2$, $X_3$, and $X_4$ is F or a group of atoms containing at least one fluorine atom.

While all of the compounds of this invention are useful, certain classes are preferred. The following paragraphs describe certain preferred classes of a compound of formula I, wherein:

a) at least one of $X_1$, $X_2$, $X_3$, and $X_4$ is selected from F, $CF_3$, $CHF_2$, $CH_2F$, $OCF_3$, $OCHF_2$, and $OCH_2F$;

b) one of $X_1$, $X_2$, $X_3$, and $X_4$ is selected from F, $CF_3$, $CHF_2$, $CH_2F$, $OCF_3$, $OCHF_2$, and $OCH_2F$;

c) one of $X_1$, $X_2$, $X_3$, and $X_4$ is selected from F, $CF_3$, $CHF_2$, $CH_2F$, $OCF_3$, $OCHF_2$, and $OCH_2F$ and the remaining $X_1$, $X_2$, $X_3$, and $X_4$ are selected from F, I and hydrogen;

d) two of $X_1$, $X_2$, $X_3$, and $X_4$ are selected from F, $CF_3$, $CHF_2$, $CH_2F$, $OCF_3$, $OCHF_2$, and $OCH_2F$ and the remaining $X_1$, $X_2$, $X_3$, and $X_4$ are selected from F, I and hydrogen; and e) at least one of $X_1$, $X_2$, $X_3$, and $X_4$ is selected from F, $CF_3$, $CHF_2$, and $CH_2F$.

In one aspect, the invention provides a compound of formula II:

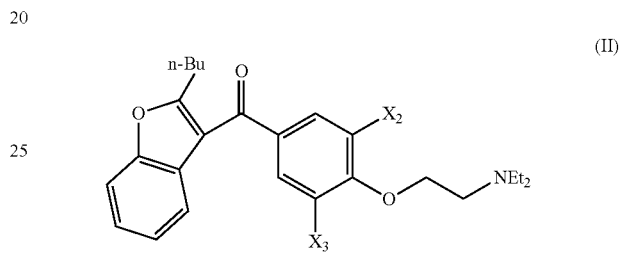

(II)

or a pharmaceutically acceptable salt or solvate thereof, wherein $X_2$ is selected from hydrogen, I, F, $CF_3$, $CHF_2$, $CH_2F$, $OCF_3$, $OCHF_2$, and $OCH_2F$;

$X_3$ is selected from hydrogen, I, F, $CF_3$, $CHF_2$, $CH_2F$, $OCF_3$, $OCHF_2$, and $OCH_2F$, provided that $X_2$ and $X_3$ are not both I. In one aspect, the invention provides a compound of formula II, provided that the compound has at least one fluorine atom or has a group of atoms containing at least one fluorine atom. In one aspect, the invention provides a compound of formula II, provided that at least one of $X_2$ and $X_3$ is F or a group of atoms containing at least one fluorine atom.

The following paragraphs describe certain preferred classes of a compound of formula II, wherein:

a-1) $X_2$ is selected from F, $CF_3$, $CHF_2$, $CH_2F$, $OCF_3$, $OCHF_2$, and $OCH_2F$ and $X_3$ is selected from F, $CF_3$, $CHF_2$, $CH_2F$, $OCF_3$, $OCHF_2$, and $OCH_2F$;

a-2) $X_2$ is $CF_3$ and $X_3$ is selected from hydrogen, I, F, $CF_3$, $CHF_2$, $CH_2F$, $OCF_3$, $OCHF_2$, and $OCH_2F$;

a-3) $X_2$ is $CF_3$ and $X_3$ is selected from $CF_3$, $CHF_2$, $CH_2F$, $OCF_3$, $OCHF_2$, and $OCH_2F$;

a-4) $X_2$ is $CF_3$ and $X_3$ is selected from $CF_3$, $CHF_2$, and $CH_2F$;

a-5) $X_2$ is $CF_3$ and $X_3$ is selected from $OCF_3$, $OCHF_2$, and $OCH_2F$;

a-6) $X_2$ is F and $X_3$ is selected from hydrogen, I, F, $CF_3$, $CHF_2$, $CH_2F$, $OCF_3$, $OCHF_2$, and $OCH_2F$;

a-7) $X_2$ is F and $X_3$ is selected from $CF_3$, $CHF_2$, $CH_2F$, $OCF_3$, $OCHF_2$, and $OCH_2F$;

a-8) $X_2$ is F and $X_3$ is selected from $CF_3$, $CHF_2$, and $CH_2F$;

a-9) $X_2$ is F and $X_3$ is selected from $OCF_3$, $OCHF_2$, and $OCH_2F$;

a-10) $X_3$ is $CF_3$ and $X_2$ is selected from hydrogen, I, F, $CF_3$, $CHF_2$, $CH_2F$, $OCF_3$, $OCHF_2$, and $OCH_2F$;

a-11) $X_3$ is $CF_3$ and $X_2$ is selected from $CF_3$, $CHF_2$, $CH_2F$, $OCF_3$, $OCHF_2$, and $OCH_2F$;

a-12) $X_3$ is $CF_3$ and $X_2$ is selected from $CF_3$, $CHF_2$, and $CH_2F$;
a-13) $X_3$ is $CF_3$ and $X_2$ is selected from $OCF_3$, $OCHF_2$, and $OCH_2F$;
a-14) $X_3$ is F and $X_2$ is selected from hydrogen, I, F, $CF_3$, $CHF_2$, $CH_2F$, $OCF_3$, $OCHF_2$, and $OCH_2F$;
a-15) $X_3$ is F and $X_2$ is selected from $CF_3$, $CHF_2$, $CH_2F$, $OCF_3$, $OCHF_2$, and $OCH_2F$;
a-16) $X_3$ is F and $X_2$ is selected from $CF_3$, $CHF_2$, and $CH_2F$;
a-17) $X_3$ is F and $X_2$ is selected from $OCF_3$, $OCHF_2$, and $OCH_2F$;
a-18) $X_2$ is $CF_3$ and $X_3$ is selected from hydrogen, I, F, $CF_3$, $CHF_2$, and $CH_2F$;
a-19) $X_2$ is $CF_3$ and $X_3$ is selected from hydrogen, I, and $CF_3$.
a-20) $X_3$ is hydrogen and $X_2$ is selected from F, $CF_3$, $CHF_2$, $CH_2F$, $OCF_3$, $OCHF_2$, and $OCH_2F$.
a-21) $X_3$ is hydrogen and $X_2$ is selected from F, $CF_3$, $CHF_2$, and $CH_2F$.
a-22) $X_3$ is hydrogen and $X_2$ is selected from F and $CF_3$.

In one aspect, the invention provides a compound of formula III:

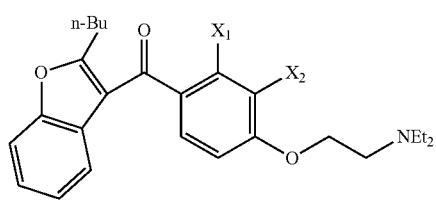

(III)

or a pharmaceutically acceptable salt or solvate thereof, wherein
$X_1$ is selected from hydrogen, I, F, $CF_3$, $CHF_2$, $CH_2F$, $OCF_3$, $OCHF_2$, and $OCH_2F$; and
$X_2$ is selected from hydrogen, I, F, $CF_3$, $CHF_2$, $CH_2F$, $OCF_3$, $OCHF_2$, and $OCH_2F$. In one aspect, the invention provides a compound of formula III, provided that the compound has at least one fluorine atom or has a group of atoms containing at least one fluorine atom. In one aspect, the invention provides a compound of formula III, provided that at least one of $X_1$ and $X_2$ is F or a group of atoms containing at least one fluorine atom.

The following paragraphs describe certain preferred classes of a compound of formula III, wherein:
b-1) $X_1$ is selected from F, $CF_3$, $CHF_2$, $CH_2F$, $OCF_3$, $OCHF_2$, and $OCH_2F$ and $X_2$ is selected from I, F, $CF_3$, $CHF_2$, $CH_2F$, $OCF_3$, $OCHF_2$, and $OCH_2F$;
b-2) $X_2$ is I and $X_1$ is selected from F, $CF_3$, $CHF_2$, $CH_2F$, $OCF_3$, $OCHF_2$, and $OCH_2F$;
b-3) $X_2$ is I and $X_1$ is selected from F, $CF_3$, $CHF_2$, and $CH_2F$;
b-4) $X_1$ is selected from F, $CF_3$, $CHF_2$, $CH_2F$, $OCF_3$, $OCHF_2$, and $OCH_2F$ and $X_2$ is selected from F, $CF_3$, $CHF_2$, $CH_2F$, $OCF_3$, $OCHF_2$, and $OCH_2F$;
b-5) $X_1$ is $CF_3$ and $X_2$ is selected from hydrogen, I, F, $CF_3$, $CHF_2$, $CH_2F$, $OCF_3$, $OCHF_2$, and $OCH_2F$;
b-6) $X_1$ is $CF_3$ and $X_2$ is selected from $CF_3$, $CHF_2$, $CH_2F$, $OCF_3$, $OCHF_2$, and $OCH_2F$;
b-7) $X_1$ is $CF_3$ and $X_2$ is selected from $CF_3$, $CHF_2$, and $CH_2F$;
b-8) $X_1$ is $CF_3$ and $X_2$ is selected from $OCF_3$, $OCHF_2$, and $OCH_2F$;
b-9) $X_1$ is F and $X_2$ is selected from hydrogen, I, F, $CF_3$, $CHF_2$, $CH_2F$, $OCF_3$, $OCHF_2$, and $OCH_2F$;
b-10) $X_1$ is F and $X_2$ is selected from $CF_3$, $CHF_2$, $CH_2F$, $OCF_3$, $OCHF_2$, and $OCH_2F$;
b-11) $X_1$ is F and $X_2$ is selected from $CF_3$, $CHF_2$, and $CH_2F$;
b-12) $X_1$ is F and $X_2$ is selected from $OCF_3$, $OCHF_2$, and $OCH_2F$;
b-13) $X_2$ is $CF_3$ and $X_1$ is selected from hydrogen, I, F, $CF_3$, $CHF_2$, $CH_2F$, $OCF_3$, $OCHF_2$, and $OCH_2F$;
b-14) $X_2$ is $CF_3$ and $X_1$ is selected from $CF_3$, $CHF_2$, $CH_2F$, $OCF_3$, $OCHF_2$, and $OCH_2F$;
b-15) $X_2$ is $CF_3$ and $X_1$ is selected from $CF_3$, $CHF_2$, and $CH_2F$;
b-16) $X_2$ is $CF_3$ and $X_1$ is selected from $OCF_3$, $OCHF_2$, and $OCH_2F$;
b-17) $X_2$ is F and $X_1$ is selected from hydrogen, I, F, $CF_3$, $CHF_2$, $CH_2F$, $OCF_3$, $OCHF_2$, and $OCH_2F$;
b-18) $X_2$ is F and $X_1$ is selected from $CF_3$, $CHF_2$, $CH_2F$, $OCF_3$, $OCHF_2$, and $OCH_2F$;
b-19) $X_2$ is F and $X_1$ is selected from $CF_3$, $CHF_2$, and $CH_2F$; and
b-20) $X_2$ is F and $X_1$ is selected from $OCF_3$, $OCHF_2$, and $OCH_2F$;

In one aspect, the invention provides a compound of formula IV:

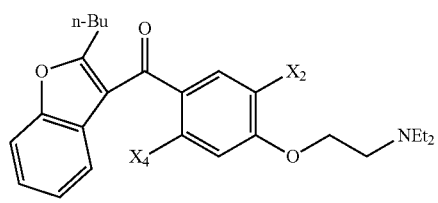

(IV)

or a pharmaceutically acceptable salt or solvate thereof, wherein
$X_2$ is selected from hydrogen, I, F, $CF_3$, $CHF_2$, $CH_2F$, $OCF_3$, $OCHF_2$, and $OCH_2F$; and
$X_4$ is selected from hydrogen, I, F, $CF_3$, $CHF_2$, $CH_2F$, $OCF_3$, $OCHF_2$, and $OCH_2F$. In one aspect, the invention provides a compound of formula IV, provided that the compound has at least one fluorine atom or has a group of atoms containing at least one fluorine atom. In one aspect, the invention provides a compound of formula IV, provided that at least one of $X_2$ and $X_4$ is F or a group of atoms containing at least one fluorine atom.

The following paragraphs describe certain preferred classes of a compound of formula IV, wherein:
c-1) $X_2$ is selected from I, F, $CF_3$, $CHF_2$, $CH_2F$, $OCF_3$, $OCHF_2$, and $OCH_2F$ and $X_4$ is selected from I, F, $CF_3$, $CHF_2$, $CH_2F$, $OCF_3$, $OCHF_2$, and $OCH_2F$;
c-2) $X_2$ is I and $X_4$ is selected from F, $CF_3$, $CHF_2$, $CH_2F$, $OCF_3$, $OCHF_2$, and $OCH_2F$;
c-3) $X_2$ is selected from F, $CF_3$, $CHF_2$, $CH_2F$, $OCF_3$, $OCHF_2$, and $OCH_2F$ and $X_4$ is selected from F, $CF_3$, $CHF_2$, $CH_2F$, $OCF_3$, $OCHF_2$, and $OCH_2F$;
c-4) $X_2$ is $CF_3$ and $X_4$ is selected from hydrogen, I, F, $CF_3$, $CHF_2$, $CH_2F$, $OCF_3$, $OCHF_2$, and $OCH_2F$;
c-5) $X_2$ is $CF_3$ and $X_4$ is selected from $CF_3$, $CHF_2$, $CH_2F$, $OCF_3$, $OCHF_2$, and $OCH_2F$;
c-6) $X_2$ is $CF_3$ and $X_4$ is selected from $CF_3$, $CHF_2$, and $CH_2F$;
c-7) $X_2$ is $CF_3$ and $X_4$ is selected from $OCF_3$, $OCHF_2$, and $OCH_2F$;
c-8) $X_2$ is F and $X_4$ is selected from hydrogen, I, F, $CF_3$, $CHF_2$, $CH_2F$, $OCF_3$, $OCHF_2$, and $OCH_2F$;

c-9) $X_2$ is F and $X_4$ is selected from $CF_3$, $CHF_2$, $CH_2F$, $OCF_3$, $OCHF_2$, and $OCH_2F$;
c-10) $X_2$ is F and $X_4$ is selected from $CF_3$, $CHF_2$, and $CH_2F$;
c-11) $X_2$ is F and $X_4$ is selected from $OCF_3$, $OCHF_2$, and $OCH_2F$;
c-12) $X_4$ is $CF_3$ and $X_2$ is selected from hydrogen, I, F, $CF_3$, $CHF_2$, $CH_2F$, $OCF_3$, $OCHF_2$, and $OCH_2F$;
c-13) $X_4$ is $CF_3$ and $X_2$ is selected from $CF_3$, $CHF_2$, $CH_2F$, $OCF_3$, $OCHF_2$, and $OCH_2F$;
c-14) $X_4$ is $CF_3$ and $X_2$ is selected from $CF_3$, $CHF_2$, and $CH_2F$;
c-15) $X_4$ is $CF_3$ and $X_2$ is selected from $OCF_3$, $OCHF_2$, and $OCH_2F$;
c-16) $X_4$ is F and $X_2$ is selected from hydrogen, I, F, $CF_3$, $CHF_2$, $CH_2F$, $OCF_3$, $OCHF_2$, and $OCH_2F$;
c-17) $X_4$ is F and $X_2$ is selected from $CF_3$, $CHF_2$, $CH_2F$, $OCF_3$, $OCHF_2$, and $OCH_2F$;
c-18) $X_4$ is F and $X_2$ is selected from $CF_3$, $CHF_2$, and $CH_2F$; and
c-19) $X_4$ is F and $X_2$ is selected from $OCF_3$, $OCHF_2$, and $OCH_2F$.

In one aspect, the invention provides a compound of formula V:

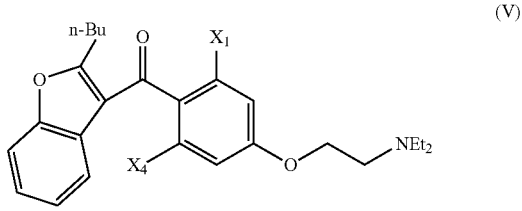

or a pharmaceutically acceptable salt or solvate thereof, wherein
$X_1$ is selected from hydrogen, I, F, $CF_3$, $CHF_2$, $CH_2F$, $OCF_3$, $OCHF_2$, and $OCH_2F$; and
$X_4$ is selected from hydrogen, I, F, $CF_3$, $CHF_2$, $CH_2F$, $OCF_3$, $OCHF_2$, and $OCH_2F$. In one aspect, the invention provides a compound of formula V, provided that the compound has at least one fluorine atom or has a group of atoms containing at least one fluorine atom. In one aspect, the invention provides a compound of formula V, and provided that at least one of $X_1$ and $X_4$ is F or a group of atoms containing at least one fluorine atom.

The following paragraphs describe certain preferred classes of a compound of formula V, wherein:
d-1) $X_1$ is selected from I, F, $CF_3$, $CHF_2$, $CH_2F$, $OCF_3$, $OCHF_2$, and $OCH_2F$ and $X_4$ is selected from I, F, $CF_3$, $CHF_2$, $CH_2F$, $OCF_3$, $OCHF_2$, and $OCH_2F$;
d-2) $X_1$ is selected from F, $CF_3$, $CHF_2$, $CH_2F$, $OCF_3$, $OCHF_2$, and $OCH_2F$ and $X_4$ is selected from F, $CF_3$, $CHF_2$, $CH_2F$, $OCF_3$, $OCHF_2$, and $OCH_2F$;
d-3) $X_1$ is $CF_3$ and $X_4$ is selected from hydrogen, I, F, $CF_3$, $CHF_2$, $CH_2F$, $OCF_3$, $OCHF_2$, and $OCH_2F$;
d-4) $X_1$ is $CF_3$ and $X_4$ is selected from $CF_3$, $CHF_2$, $CH_2F$, $OCF_3$, $OCHF_2$, and $OCH_2F$;
d-5) $X_1$ is $CF_3$ and $X_4$ is selected from $CF_3$, $CHF_2$, and $CH_2F$;
d-6) $X_1$ is $CF_3$ and $X_4$ is selected from $OCF_3$, $OCHF_2$, and $OCH_2F$;
d-7) $X_1$ is F and $X_4$ is selected from hydrogen, I, F, $CF_3$, $CHF_2$, $CH_2F$, $OCF_3$, $OCHF_2$, and $OCH_2F$;
d-8) $X_1$ is F and $X_4$ is selected from $CF_3$, $CHF_2$, $CH_2F$, $OCF_3$, $OCHF_2$, and $OCH_2F$;
d-9) $X_1$ is F and $X_4$ is selected from $CF_3$, $CHF_2$, and $CH_2F$;
d-10) $X_1$ is F and $X_4$ is selected from $OCF_3$, $OCHF_2$, and $OCH_2F$;
d-11) $X_4$ is $CF_3$ and $X_1$ is selected from hydrogen, I, F, $CF_3$, $CHF_2$, $CH_2F$, $OCF_3$, $OCHF_2$, and $OCH_2F$;
d-12) $X_4$ is $CF_3$ and $X_1$ is selected from $CF_3$, $CHF_2$, $CH_2F$, $OCF_3$, $OCHF_2$, and $OCH_2F$;
d-13) $X_4$ is $CF_3$ and $X_1$ is selected from $CF_3$, $CHF_2$, and $CH_2F$;
d-14) $X_4$ is $CF_3$ and $X_1$ is selected from $OCF_3$, $OCHF_2$, and $OCH_2F$;
d-15) $X_4$ is F and $X_1$ is selected from hydrogen, I, F, $CF_3$, $CHF_2$, $CH_2F$, $OCF_3$, $OCHF_2$, and $OCH_2F$;
d-16) $X_4$ is F and $X_1$ is selected from $CF_3$, $CHF_2$, $CH_2F$, $OCF_3$, $OCHF_2$, and $OCH_2F$;
d-17) $X_4$ is F and $X_1$ is selected from $CF_3$, $CHF_2$, and $CH_2F$; and
d-18) $X_4$ is F and $X_1$ is selected from $OCF_3$, $OCHF_2$, and $OCH_2F$.

In one aspect, the invention provides a compound of formula VI:

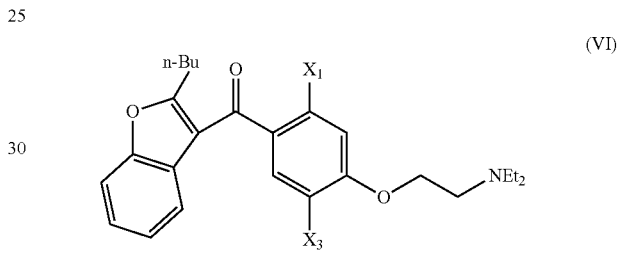

or a pharmaceutically acceptable salt or solvate thereof, wherein
$X_1$ is selected from hydrogen, I, F, $CF_3$, $CHF_2$, $CH_2F$, $OCF_3$, $OCHF_2$, and $OCH_2F$; and
$X_4$ is selected from hydrogen, I, F, $CF_3$, $CHF_2$, $CH_2F$, $OCF_3$, $OCHF_2$, and $OCH_2F$. In one aspect, the invention provides a compound of formula VI, provided that at least one fluorine atom or has a group of atoms containing at least one fluorine atom. In one aspect, the invention provides a compound of formula VI, provided that at least one of $X_1$ and $X_3$ is F or a group of atoms containing at least one fluorine atom The following paragraphs describe certain preferred classes of a compound of formula VI, wherein:
e-1) $X_1$ is selected from I, F, $CF_3$, $CHF_2$, $CH_2F$, $OCF_3$, $OCHF_2$, and $OCH_2F$ and $X_3$ is selected from I, $CF_3$, $CHF_2$, $CH_2F$, $OCF_3$, $OCHF_2$, and $OCH_2F$;
e-2) $X_3$ is I and $X_1$ is selected from I, F, $CF_3$, $CHF_2$, $CH_2F$, $OCF_3$, $OCHF_2$, and $OCH_2F$;
e-3) $X_1$ is selected from F, $CF_3$, $CHF_2$, $CH_2F$, $OCF_3$, $OCHF_2$, and $OCH_2F$ and $X_3$ is selected from F, $CF_3$, $CHF_2$, $CH_2F$, $OCF_3$, $OCHF_2$, and $OCH_2F$;
e-4) $X_1$ is $CF_3$ and $X_3$ is selected from hydrogen, I, F, $CF_3$, $CHF_2$, $CH_2F$, $OCF_3$, $OCHF_2$, and $OCH_2F$;
e-5) $X_1$ is $CF_3$ and $X_3$ is selected from $CF_3$, $CHF_2$, $CH_2F$, $OCF_3$, $OCHF_2$, and $OCH_2F$;
e-6) $X_1$ is $CF_3$ and $X_3$ is selected from $CF_3$, $CHF_2$, and $CH_2F$;
e-7) $X_1$ is $CF_3$ and $X_3$ is selected from $OCF_3$, $OCHF_2$, and $OCH_2F$;
e-8) $X_1$ is F and $X_3$ is selected from hydrogen, I, F, $CF_3$, $CHF_2$, $CH_2F$, $OCF_3$, $OCHF_2$, and $OCH_2F$;

e-9) $X_1$ is F and $X_3$ is selected from $CF_3$, $CHF_2$, $CH_2F$, $OCF_3$, $OCHF_2$, and $OCH_2F$;
e-10) $X_1$ is F and $X_3$ is selected from $CF_3$, $CHF_2$, and $CH_2F$;
e-11) $X_1$ is F and $X_3$ is selected from $OCF_3$, $OCHF_2$, and $OCH_2F$;
e-12) $X_3$ is $CF_3$ and $X_1$ is selected from hydrogen, I, F, $CF_3$, $CHF_2$, $CH_2F$, $OCF_3$, $OCHF_2$, and $OCH_2F$;
e-13) $X_3$ is $CF_3$ and $X_1$ is selected from $CF_3$, $CHF_2$, $CH_2F$, $OCF_3$, $OCHF_2$, and $OCH_2F$;
e-14) $X_3$ is $CF_3$ and $X_1$ is selected from $CF_3$, $CHF_2$, and $CH_2F$;
e-15) $X_3$ is $CF_3$ and $X_1$ is selected from $OCF_3$, $OCHF_2$, and $OCH_2F$;
e-16) $X_3$ is F and $X_1$ is selected from hydrogen, I, F, $CF_3$, $CHF_2$, $CH_2F$, $OCF_3$, $OCHF_2$, and $OCH_2F$;
e-17) $X_3$ is F and $X_1$ is selected from $CF_3$, $CHF_2$, $CH_2F$, $OCF_3$, $OCHF_2$, and $OCH_2F$;
e-18) $X_3$ is F and $X_1$ is selected from $CF_3$, $CHF_2$, and $CH_2F$; and
e-19) $X_3$ is F and $X_1$ is selected from $OCF_3$, $OCHF_2$, $OCH_2F$.

In one aspect, the invention provides a compound of formula VII:

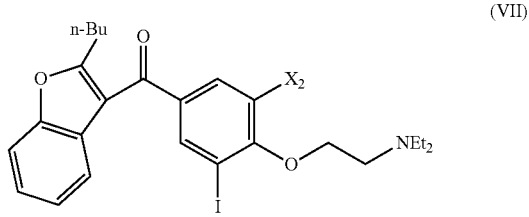

(VII)

or a pharmaceutically acceptable salt or solvate thereof, wherein
$X_2$ is selected from F, $CF_3$, $CHF_2$, $CH_2F$, $OCF_3$, $OCHF_2$, and $OCH_2F$.

The following paragraphs describe certain preferred classes of a compound of formula VII, wherein:
f-1) $X_2$ is selected from F, $CF_3$, $CHF_2$, and $CH_2F$;
f-2) $X_2$ is selected from F and $CF_3$;
f-3) $X_2$ is selected from $CF_3$, $CHF_2$, and $CH_2F$;
f-4) $X_2$ is selected from F, $OCF_3$, $OCHF_2$, and $OCH_2F$;
f-5) $X_2$ is selected from F and $OCF_3$; and
f-6) $X_2$ is selected from $OCF_3$, $OCHF_2$, and $OCH_2F$.

In one aspect, the invention provides a compound of formula VIII:

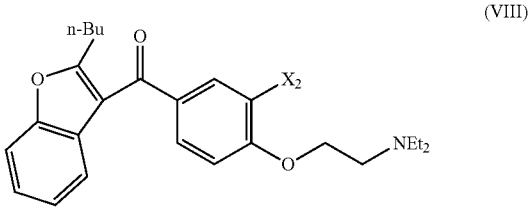

(VIII)

or a pharmaceutically acceptable salt or solvate thereof, wherein
$X_2$ is selected from F, $CF_3$, $CHF_2$, $CH_2F$, $OCF_3$, $OCHF_2$, and $OCH_2F$.

The following paragraphs describe certain preferred classes of a compound of formula VIII, wherein:

g-1) $X_2$ is selected from $CF_3$, $CHF_2$, $CH_2F$, $OCF_3$, $OCHF_2$, and $OCH_2F$;
g-2) $X_2$ is selected from F, $CF_3$, $CHF_2$, and $CH_2F$;
g-3) $X_2$ is selected from F and $CF_3$;
g-4) $X_2$ is selected from $CF_3$, $CHF_2$, and $CH_2F$;
g-5) $X_2$ is selected from F, $OCF_3$, $OCHF_2$, and $OCH_2F$;
g-6) $X_2$ is selected from F and $OCF_3$; and
g-7) $X_2$ is selected from $OCF_3$, $OCHF_2$, and $OCH_2F$.

In one aspect, the invention provides a compound of formula IX:

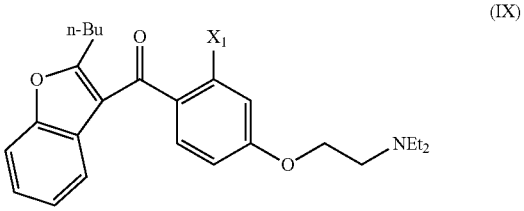

(IX)

or a pharmaceutically acceptable salt or solvate thereof, wherein
$X_1$ is selected from F, $CF_3$, $CHF_2$, $CH_2F$, $OCF_3$, $OCHF_2$, and $OCH_2F$;

The following paragraphs describe certain preferred classes of a compound of formula IX, wherein:
h-1) $X_1$ is selected from $CF_3$, $CHF_2$, $CH_2F$, $OCF_3$, $OCHF_2$, and $OCH_2F$;
h-2) $X_1$ is selected from F, $CF_3$, $CHF_2$, and $CH_2F$;
h-3) $X_1$ is selected from F and $CF_3$;
h-4) $X_1$ is selected from $CF_3$, $CHF_2$, and $CH_2F$;
h-5) $X_1$ is selected from F, $OCF_3$, $OCHF_2$, and $OCH_2F$;
h-6) $X_1$ is selected from F and $OCF_3$; and
h-7) $X_1$ is selected from $OCF_3$, $OCHF_2$, and $OCH_2F$.

In one aspect, the invention provides a compound of Table 1.

TABLE 1

| Compound # | |
|---|---|
| 1 | ![structure 1] |
| 2 | ![structure 2] |
| 3 | ![structure 3] |

TABLE 1-continued

| Compound # | Structure |
|---|---|
| 4 | 2-n-Bu-benzofuran-3-yl connected via C(=O) to phenyl bearing 2-CF₃ and 4-O-CH₂CH₂-NEt₂ |
| 5 | 2-n-Bu-benzofuran-3-yl connected via C(=O) to phenyl bearing 2-CF₃, 3-CF₃ and 4-O-CH₂CH₂-NEt₂ |
| 6 | 2-n-Bu-benzofuran (with 7-CF₃) connected via C(=O) to phenyl bearing 3-CF₃ and 4-O-CH₂CH₂-NEt₂ |
| 7 | 2-n-Bu-benzofuran (with 7-CF₃) connected via C(=O) to phenyl bearing 2-CF₃, 6-CF₃ and 4-O-CH₂CH₂-NEt₂ |
| 8 | 2-n-Bu-benzofuran-3-yl connected via C(=O) to phenyl bearing 2-F and 4-O-CH₂CH₂-NEt₂ |
| 9 | 2-n-Bu-benzofuran-3-yl connected via C(=O) to phenyl bearing 3-F, 5-I and 4-O-CH₂CH₂-NEt₂ |
| 10 | 2-n-Bu-benzofuran-3-yl connected via C(=O) to phenyl bearing 3-F, 5-F and 4-O-CH₂CH₂-NEt₂ |
| 11 | 2-n-Bu-benzofuran-3-yl connected via C(=O) to phenyl bearing 3-F and 4-O-CH₂CH₂-NEt₂ |
| 12 | 2-n-Bu-benzofuran-3-yl connected via C(=O) to phenyl bearing 2-F, 5-F and 4-O-CH₂CH₂-NEt₂ |
| 13 | 2-n-Bu-benzofuran-3-yl connected via C(=O) to phenyl bearing 2-F, 3-F and 4-O-CH₂CH₂-NEt₂ |
| 14 | 2-n-Bu-benzofuran (with 7-F) connected via C(=O) to phenyl bearing 2-F, 5-F and 4-O-CH₂CH₂-NEt₂ |

In one aspect, a compound of the invention is a pharmaceutically acceptable salt. In one aspect, a compound of the invention is a solvate. In one aspect, a compound of the invention is a hydrate.

The present invention relates to pharmaceutical compositions comprising one of the compounds of the invention as an active ingredient. In one aspect, the invention provides a pharmaceutical composition comprising at least one compound of formulae I, II, III, IV, V, VI, VII, VIII, or IX or a pharmaceutically acceptable salt or solvate thereof and one or more pharmaceutically acceptable carrier or excipient. In one aspect, the invention provides a pharmaceutical composition comprising at least one compound of Table 1.

The present invention relates to a method of synthesizing a compound of the invention or a pharmaceutically acceptable salt or solvate thereof. A compound of the invention can be synthesized using a variety of methods known in the art. The scheme and description below depicts some general routes for the preparation of a compound of the invention.

Scheme 1A

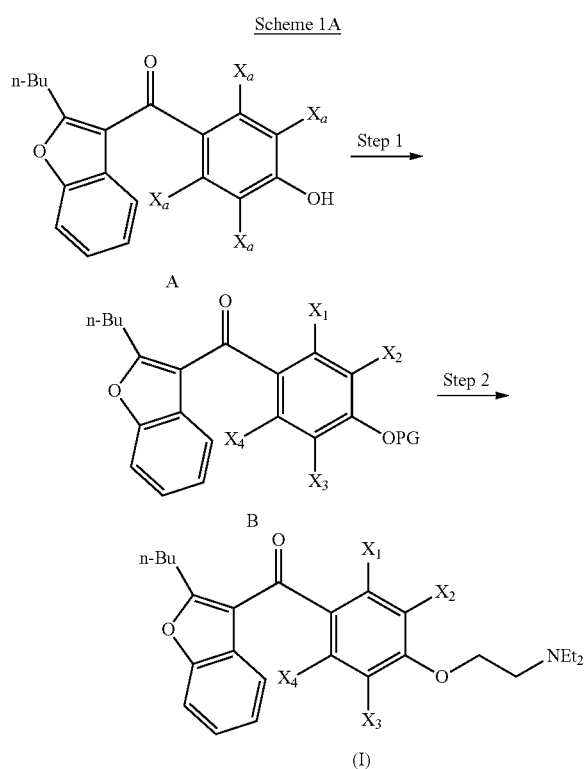

Scheme 1A outlines a preparation for a compound of Formula I. It is understood that Formulae II, III, IV, V, VI, VII, VIII, and IX described herein are subsets of Formula I. Thus, the preparations described for a compound of Formula I can also be applied for the preparation of a compound of Formulae II, III, IV, V, VI, VII, VIII, and IX.

In Scheme 1A, the preparation begins with Compound A. Compounds such as Compound A are commercially available, for example the compound wherein $X_a$ is H is available from multiple chemical supply sources. In Step 1, the hydroxyl group of Compound A is protected with a suitable protecting group (PG) to form Compound B. For example, the hydroxyl group of Compound A can be treated with pyridine-acetic anhydride and DMAP, to form compound B, where PG is acetyl. Examples of additional protecting groups are described by T. W. Greene, "Protective Groups in Organic Synthesis", John Wiley and Sons, New York, N.Y., Fourth Edition. In Step 1, after protection of the hydroxyl group, at least one $X_a$ of Compound A is converted to a fluorine atom or a fluorine containing group. For example, at least one $X_a$ of Compound A can be an iodine atom that is converted to fluorine or a fluorine containing group to form Compound B. Compound A can be treated with methyl fluorosulfonyldifluoroacetate and CuI to form Compound B, such that one $X_a$ is converted to the fluorine containing group is $CF_3$. It is noted that one or more $X_a$ of Compound A may not change in Step 1 e.g., $X_a$ is $X_1$, wherein $X_1$ is hydrogen.

In Step 2, PG of Compound B is deprotected and the resulting hydroxyl group is alkylated to form a compound of Formula I. PG can be deprotected using a variety of conditions known in the art. In one aspect, the deprotection conditions can be basic. For example, when PG is acetyl, PG can be deprotected using potassium carbonate and methanol. The deprotected hydroxyl group can be alkylated using a variety of different methods to form a compound of Formula I. For example, the hydroxyl group can be alkylated with 2-chloro-N,N-diethylanamine using NaI and $K_2CO_3$.

If any or more of $X_1$, $X_2$, $X_3$, or $X_4$ of Compound B is an iodine atom, the iodine atom can be replaced with a hydrogen atom. For example, the iodine atom can be reduced using zinc powder in acetic acid.

If one of the $X_a$ of Compound A contains a fluorine atom or a fluorine containing group, the hydroxyl group of Compound A can be directly alkylated to form a compound of Formula I. For example, Compound A can be alkylated with 2-chloro-N,N-diethylanamine using NaI and $K_2CO_3$ as reagents to form compound C.

The present invention also comprehends deuterium labeled compounds, which are identical to those recited in formulae I, II, III, IV, V, VI, VII, VIII, or IX and the compounds listed in Table 1 but for the fact that one or more hydrogen atoms is replaced by a deuterium atom having an abundance of deuterium at that position that is substantially greater than the natural abundance of deuterium, which is 0.015%.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

A compound of the invention or a pharmaceutically acceptable salt or solvate thereof that contains the aforementioned deuterium atom(s) is within the scope of the invention. Further, substitution with heavier deuterium, i.e., $^2$H, can afford certain therapeutic advantages resulting from greater metabolic stability, for example increased in vivo half-life or reduced dosage requirements.

In one aspect, the invention provides a deuterium labeled compound of Table 2.

TABLE 2

| Compound # |
|---|
| 15 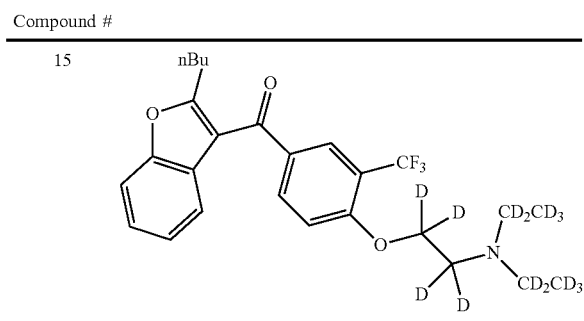 |

In one aspect, a deuterium labeled compound of the invention is a pharmaceutically acceptable salt. In one aspect, a deuterium labeled compound of the invention is a solvate. In one aspect, a deuterium labeled compound of the invention is a hydrate.

The present invention relates to pharmaceutical compositions comprising one of the deuterium labeled compounds of the invention as an active ingredient. In one aspect, the invention provides a pharmaceutical composition comprising at least one deuterium labeled compound of formulae I, II, III, IV, V, VI, VII, VIII, or IX or a pharmaceutically acceptable salt or solvate thereof and one or more pharmaceutically acceptable carrier or excipient. In one aspect, the invention provides a pharmaceutical composition comprising at least one compound of Table 2.

The present invention relates to a method of synthesizing a deuterium labeled compound of the invention or a pharmaceutically acceptable salt or solvate thereof.

The deuterium labeled compounds of the invention can be prepared using any of a variety of art-recognized techniques. The deuterium labeled compounds can generally be prepared by carrying out the procedures disclosed in Scheme 1A and the description provided herein for the preparation of a compound of Formula I. For example, a deuterium labeled compound can be prepared by starting with deuterium labeled Compound A and/or substituting a readily available deuterium labeled reagent for a non-deuterium labeled reagent.

Methods of Use

The present invention relates to methods for the use of compounds of the invention. The compounds of the invention have a useful pharmacological activity spectrum and are therefore particularly suitable for the prophylaxis and/or treatment of disorders.

The present invention provides the use of a compound of the invention for the preparation of a medicament for administration to a subject for use in the treatment or prevention of disorders.

In one aspect, the invention relates to methods for use in the treatment or prevention of arrhythmias, including tachycardias and bradycardia, and/or other conditions including less severe ventricular arrhythmias and many superventricular arrhythmias including atrial fibrillation and reentrant tachyarrhythmias involving accessory pathways.

In one aspect, the invention provides a method of treating or preventing a pathological syndrome of the cardiovascular system in a subject comprising administering to a subject in need thereof an effective amount of a compound of the invention or a pharmaceutically acceptable salt thereof.

In one aspect, the invention provides a method for the treatment or prevention of cardiac arrhythmias, the potentialities offered by delayed conduction of the electrical impulse at the cardiac cell or the prolongation of the refractory period.

Although many physiopathological states prolong the repolarization of the cardiac cell and are associated with a reduced incidence of cardiac fibrillation, the concept of pharmacological control of rhythmic disorders by increasing the action potential is relatively new.

The action potential of the myocardiac cell in fact represents a modification of the resting potential of this cell which, after having attained the threshold potential (−70 millivolts) sufficiently rapidly, initiates a sequence of changes in the membrane potential.

After passage of the impulse, the myocardium remains transiently insensitive to a new stimulation; during the absolute refractory period it is absolutely impossible to excite the myocardium whereas during the relative refractory period a sufficiently powerful stimulus can lead to a slowly propagated response. The existence of the refractory periods determines the unidirectional nature of the propagation of the impulse.

The characteristics of the action potential determine those of the conduction and the refractory periods. Consequently, any shortening of the repolarization is arrhythmogenic as a result of the concomitant shortening of the refractory period. Conversely, any interference uniformly lengthening the action potential produces a lengthening of the absolute refractory period and this diminishes the arythmogenicity.

In other words, if the attainment of a threshold level of the membrane potential necessary to generate a second action potential is delayed, in response to a stimulus, by interfering in processes which normally control the rate of repolarization, the refractory periods (absolute period and efficacious period) of the cardiac muscle ought to be correspondingly prolonged, a phenomenon which would be expected to create an antiarrhythmic mechanism.

At present, amiodarone or 2-n-butyl 3-[4-(2-diethylamino ethoxy) 3,5-diiodo benzoyl]benzofuran is one of the rare anti-arrhythmic agents on the market which possesses the properties explained above.

The compound, in fact, prolongs the repolarization plateau without modifying the rate of rapid depolarization. Its anti-arrhythmic effect derives from the uniform lengthening of the action potentials and the refractory periods of the myocardial cells.

Furthermore, amiodarone possesses incomplete anti-adrenergic properties of the α- and β-types. Hence, this compound may be considered not as a β-blocker but as an adreno-decelerator, i.e. as a partial antagonist of α- and β-adrenergic reactions. Such properties are of indisputable benefit since it appears desirable not to look for complete α- or β-antagonistic properties in view of the side effects to which they may lead in the clinic ("Bruxelles Medical", No. 9, September 1969, pages 543-560).

In one aspect, a compound of the invention possesses remarkable pharmacological properties which are expressed in particular by an increase in the duration of the action potential and the refractory periods of the cardiac cell.

Amiodarone possess unwanted side effects. In particular, it is known that amiodarone causes phospholipidoses in the lung, which results in the destruction of macrophages in the alveoli. This destruction is expressed in the patient undergoing treatment with amiodarone by the appearance of pulmonary complications, such as respiratory insufficiency which will require the cessation of treatment. In one aspect, a compound of the invention possesses fewer side effects than amiodarone.

In one aspect, the invention provides a method of treating or preventing arrhythmias in a subject comprising administering to the subject in need thereof an effective amount of a compound of the invention or a pharmaceutically acceptable salt thereof. There are two major types of arrhythmias are tachycardias (the heartbeat is too fast—more than 100 beats per minute), and bradycardia (the heartbeat is too slow—less than 60 beats per minute). Arrhythmias can be life-threatening if they cause a severe decrease in the pumping function of the heart. When the pumping function is severely decreased for more than a few seconds, blood circulation is essentially stopped, and organ damage (such as brain damage) may occur within a few minutes. Life threatening arrhythmias include ventricular tachycardia and ventricular fibrillation.

Arrhythmias are identified by where they occur in the heart (atria or ventricles) and by what happens to the heart's rhythm when they occur.

Arrhythmias that start in the atria are called atrial or supraventricular (above the ventricles) arrhythmias. Ventricular arrhythmias begin in the ventricles. Ventricular arrhythmias are usually caused by heart disease are very serious.

Arrhythmias Originating in the Atria include:
1. Atrial fibrillation: In atrial fibrillation, the electrical activity of the heart is uncoordinated, with electricity traveling about the upper chambers in a chaotic fashion, causing the upper chambers to quiver (like a "bag of worms") and contract inefficiently or not at all. Atrial fibrillation is common particularly in the elderly and those with heart disease. It is also common in patients with heart valve disease who may require surgery to repair or replace the mitral valve.
2. Atrial flutter: Atrial flutter causes a rapid but coordinated electrical stimulation of the upper chamber of the heart, often leading to a rapid pulse. The atria are stimulated so quickly that they cannot contract or squeeze. This arrhythmia is due to a loop of electricity in the upper chambers of the heart.
3. Supraventricular tachycardias (PSVT): This is a fast heart rhythms from the top part of the heart. In this condition, repeated periods of very fast heartbeats begin and end suddenly. These arrhythmias are usually due to extra connections between the upper and lower chambers of the heart. They are often difficult to control with medication.
4. Wolff-Parkinson-White syndrome: This is a special type of Paroxysmal supraventricular tachycardia (PSVT). This syndrome involves episodes of a rapid heart rate (tachycardia) caused by abnormal electrical connection in the heart. In people with Wolff-Parkinson-White syndrome, there is an extra (accessory) connection between the top and bottom chambers of the heart. Wolff-Parkinson-White occurs in approximately 4 out of 100,000 people, and is one of the most common causes of fast heart rate disorders (tachyarrhymthmias) in infants and children.
5. Premature supraventricular contraction or premature atrial contraction (PAC): Premature beats or extra beats frequently cause irregular heart rhythms. Those that start in the upper chambers are called premature atrial contractions (PACs). These are quite common and are benign.
6. Sick sinus syndrome: The sinus node (heart's pacemaker) does not fire its signals properly, so that the heart rate slows down. Sometimes the rate changes back and forth between a slow (bradycardia) and fast (tachycardia) rate. This most often occurs in the elderly as a result of degenerative changes to the conduction pathways of the heart.
7. Sinus arrhythmia: Cyclic changes in the heart rate during breathing. Common in children and often found in normal, healthy adults. In one aspect, a pacemaker may be required for treatment.
8. Sinus tachycardia: The sinus node sends out electrical signals faster than usual, speeding up the heart rate. This is a normal response to exercise.
9. Multifocal atrial tachycardia: In multifocal atrial tachycardia (M.A.T.), multiple locations within the atria "fire" and initiate an electrical impulse. Most of these impulses are conducted to the ventricles, leading to a rapid heart rate, anywhere from 100 to 250 beats per minute. M.A.T. is most common in people 50 years old and over and it is often seen in patients with lung disease.

Arrhythmias Originating in the Ventricles include:
1. Premature ventricular contraction (PVC): An electrical signal from the ventricles causes an early heartbeat that generally goes unnoticed. The heart then seems to pause until the next beat of the ventricle occurs in a regular fashion. These are commonly detected in normal, healthy adults.
2. Ventricular Fibrillation is where electrical signals in the ventricles fire in a very fast and uncontrolled manner. This causes the lower chambers to quiver, and not pump blood. If the person does not receive immediate medical attention and a normal rhythm is not restored quickly, the patient will suffer brain and heart damage and die. Patients who survive this should have a defibrillator (ICD) implanted.
3. Ventricular Tachycarida is a rapid, regular heartbeat arising in the ventricles, the bottom chamber of the heart. When it occurs, it's usually fatal. About 400,000 people a year die from it. One treatment choice for this invariably includes an implantable defibrillator and or medication and or interventions like ablation to try to minimize or limit the number of shocks.

In aspect, the invention provides a compound of the invention that is useful in the treatment of acute life-threatening arrhythmias and/or the chronic suppression of arrhythmias. In one aspect, a compound of the invention is useful in supraventricular arrhythmias and/or ventricular arrhythmias.

In one aspect, a compound of the invention is useful for treating shock-refractory ventricular fibrillation. In one aspect, a compound of the invention is useful for treating ventricular tachycardia.

In one aspect, the invention provides a method of treating or preventing angina pectoris in a subject comprising administering to the subject in need thereof an effective amount of a compound of the invention or a pharmaceutically acceptable salt thereof.

In one aspect, the invention provides a method of treating or preventing hypertension in a subject comprising administering to the subject in need thereof an effective amount of a compound of the invention or a pharmaceutically acceptable salt thereof.

In one aspect, the invention provides a method treating or preventing cerebral circulatory insufficiency in a subject comprising administering to the subject in need thereof an effective amount of a compound of the invention or a pharmaceutically acceptable salt thereof.

In one aspect, the invention provides a method of treating or preventing a pathological syndrome of the cardiovascular system, wherein the subject is a human.

The pharmaceutical compositions of the invention may be made available in any form suitable for administration in human therapy. As regards the dosage unit, this latter may take the form, for example, of a tablet, a sugar-coated tablet, a capsule, a gelatin capsule, a powder, a suspension or a syrup for oral administration, a suppository for rectal administration and a solution or suspension for parenteral administration.

The dosage units of the pharmaceutical compositions of the invention may comprise, for example, from 50 to 500 mg by weight of the active ingredient for oral administration, from 50 to 200 mg of active ingredient for rectal administration and from 50 to 150 mg of active ingredient for parenteral administration.

Depending on the route of administration selected, the pharmaceutical compositions of the invention are prepared by combining at least one of the compounds of the invention or a pharmaceutically acceptable salt or solvate thereof with a suitable excipient, which latter may be constituted for example by at least one ingredient selected from the following substances: lactose, starches, talc, magnesium stearate, polyvinylpyrrolidone, alginic acid, collodal silica, distilled water, benzyl alcohol or sweetening agents.

In one aspect, the invention provides a medical device containing a compound of the invention or a pharmaceutically acceptable salt or solvate thereof. In one aspect, the device is a stent.

The following Examples are illustrative and should not be interpreted in any way so as to limit the scope of the invention.

EXAMPLES

Example 1

Synthesis of (2-butylbenzofuran-3-yl)(4-(2-(diethylamino)ethoxy)-3,5-bis(trifluoromethyl)phenyl)methanone (1)

4-(2-butylbenzofuran-3-carbonyl)-2-iodo-6-(trifluoromethyl)phenyl acetate and 4-(2-butylbenzofuran-3-carbonyl)-2,6-bis(trifluoromethyl)phenyl acetate

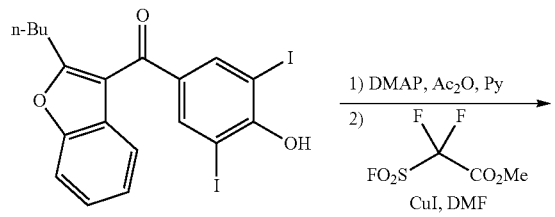

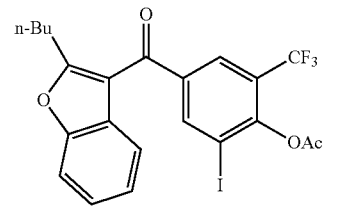

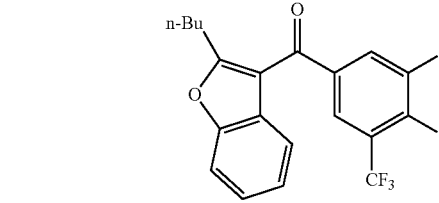

Under air, to (2-butylbenzofuran-3-yl)(4-hydroxy-3,5-diiodophenyl)methanone (2.0 g, 3.7 mmol, 1.0 equiv) in pyridine-Ac$_2$O (6 mL-6 mL) at 23° C. was added DMAP (22 mg, 0.18 mmol, 0.050 equiv). After stirring for 40 min at 23° C., 2N HCl (50 mL) was added and the solution was extracted with EtOAc (3×20 mL). The combined organic phases were washed with brine (30 mL) and dried (Na$_2$SO$_4$). The filtrate was concentrated in vacuo to afford 2.0 g of the crude acetate as yellow oil, which was used in the next step without further purification. Under nitrogen, to the crude acetate (<3.7 mmol, 1.0 equiv) in DMF (10 mL) was added CuI (1.8 g, 9.3 mmol, 2.5 equiv) and methyl fluorosulfonyldifluoroacetate (4.7 mL, 37 mmol, 10 equiv). After stirring for 40 min at 80° C., the reaction mixture was cooled to 23° C. and the precipitates were removed by filtration. The filtrate was concentrated in vacuo and H$_2$O-EtOAc (50 mL-10 mL) was added. The phases were separated and the aqueous phase was extracted with EtOAc (3×10 mL). The combined organic phases were washed with brine (30 mL) and dried (MgSO$_4$). The filtrate was concentrated in vacuo and the residue was purified by chromatography on silica gel eluting with hexanes/EtOAc to afford 843 mg of 4-(2-butylbenzofuran-3-carbonyl)-2-iodo-6-(trifluoromethyl)phenyl acetate as colorless oil (43% yield, 2 steps) and 520 mg of 4-(2-butylbenzofuran-3-carbonyl)-2,6-bis(trifluoromethyl)phenyl acetate as colorless oil (30% yield, 2 steps).

4-(2-butylbenzofuran-3-carbonyl)-2-iodo-6-(trifluoromethyl)phenyl acetate

R$_f$=0.50 (hexanes/EtOAc 9:1 (v/v)). NMR Spectroscopy: $^1$H NMR (300 MHz, CDCl$_3$, 23° C., δ): 8.46 (d, J=1.8 Hz, 1H), 8.12 (d, J=1.8 Hz, 1H), 7.51 (d, J=7.8 Hz, 1H), 7.38 (d, J=7.5 Hz, 1H), 7.33 (dd, J=7.8 Hz, 7.5 Hz, 1H), 7.25 (dd, J=7.8 Hz, 7.5 Hz, 1H), 2.88 (t, J=8.1 Hz, 2H), 2.43 (s, 3H), 1.85-1.70 (m, 2H), 1.42-1.30 (m, 2H), 0.92 (t, J=7.2 Hz, 3H). $^{19}$F NMR (281 MHz, CDCl$_3$, 23° C., δ): −61.33 (m, 3F).

4-(2-butylbenzofuran-3-carbonyl)-2,6-bis(trifluoromethyl)phenyl acetate

R$_f$=0.65 (hexanes/EtOAc 9:1 (v/v)). NMR Spectroscopy: $^1$H NMR (300 MHz, CDCl$_3$, 23° C., δ): 8.33 (s, 2H), 7.50 (d, J=7.8 Hz, 1H), 7.37 (d, J=7.5 Hz, 1H), 7.33 (dd, J=7.8 Hz, 7.5 Hz, 1H), 7.25 (dd, J=7.8 Hz, 7.5 Hz, 1H), 2.89 (t, J=8.1 Hz, 2H), 2.40 (s, 3H), 1.85-1.70 (m, 2H), 1.42-1.30 (m, 2H), 0.92 (t, J=7.2 Hz, 3H). $^{19}$F NMR (281 MHz, CDCl$_3$, 23° C., δ): −61.03 (m, 6F).

(2-butylbenzofuran-3-yl)(4-(2-(diethylamino)ethoxy)-3,5-bis(trifluoromethyl)phenyl)methanone (1)

(1)

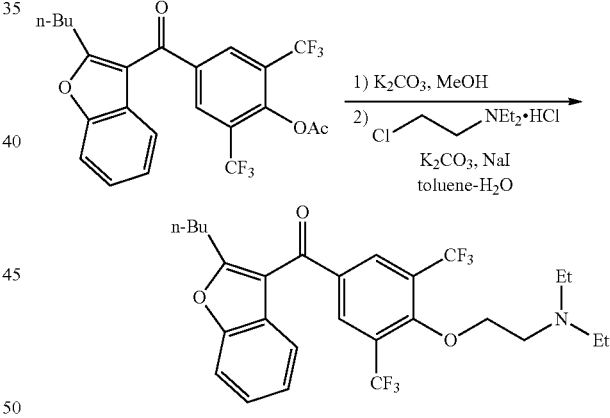

Under air, to 4-(2-butylbenzofuran-3-carbonyl)-2,6-bis(trifluoromethyl)phenyl acetate (22 mg, 0.047 mmol, 1.00 equiv) in MeOH (0.5 mL) at 23° C. was added K$_2$CO$_3$ (19 mg, 0.14 mmol, 3.0 equiv). After stirring for 1 h at 23° C., the reaction mixture was concentrated in vacuo and the residue was added 1N HCl (1 mL) and CH$_2$Cl$_2$ (1 mL). The phases were separated and the aqueous phase was extracted with CH$_2$Cl$_2$ (3×1 mL). The combined organic phases were washed with brine (3 mL) and dried (MgSO$_4$). The filtrate was concentrated in vacuo to afford 17 mg of the crude phenol as colorless oil, which was used in the next step without further purification.

Under air, to the crude phenol (<0.047 mmol, 1.0 equiv) in toluene-H$_2$O (0.8 mL-0.4 mL) at 23° C. was added NaI (0.7 mg, 0.005 mmol, 0.1 equiv), K$_2$CO$_3$ (26 mg, 0.19 mmol, 4.0 equiv), and 2-chloro-N,N-diethylethanamine (8.9 mg, 0.052 mmol, 1.1 equiv). After stirring for 45 min at 100° C., the reaction mixture was cooled to 23° C. and CH$_2$Cl$_2$ (0.5 mL) was added. The phases were separated and the aqueous phase was extracted with CH$_2$Cl$_2$ (3×0.5 mL). The combined organic phases were washed with brine (1 mL) and dried (MgSO$_4$). The filtrate was concentrated in vacuo and the residue was purified by preparative TLC eluting with hexanes/EtOAc 1:1 (v/v) to afford 14 mg of the title compound as colorless oil (56% yield, 2 steps). R$_f$=0.70 (hexanes/EtOAc 3:7 (v/v)). 8.30 (s, 2H), 7.49 (d, J=7.8 Hz, 1H), 7.37 (d, J=7.5 Hz, 1H), 7.33 (dd, J=7.8 Hz, 7.5 Hz, 1H), 7.25 (dd, J=7.8 Hz, 7.5 Hz, 1H), 4.23 (t, J=6.0 Hz, 2H), 3.04 (t, J=6.0 Hz, 2H), 2.87 (t, J=8.1 Hz, 2H), 2.71 (q, J=6.9 Hz, 4H), 1.82-1.70 (m, 2H), 1.41-1.30 (m, 2H), 1.11 (t, J=6.9 Hz, 6H), 0.90 (t, J=7.2 Hz, 3H). $^{19}$F NMR (281 MHz, CDCl$_3$, 23° C., δ): −61.02 (m, 6F).

Example 2

Synthesis of (2-butylbenzofuran-3-yl)(4-(2-(diethylamino)ethoxy)-3-iodo-5-(trifluoromethyl)phenyl)methasone (2)

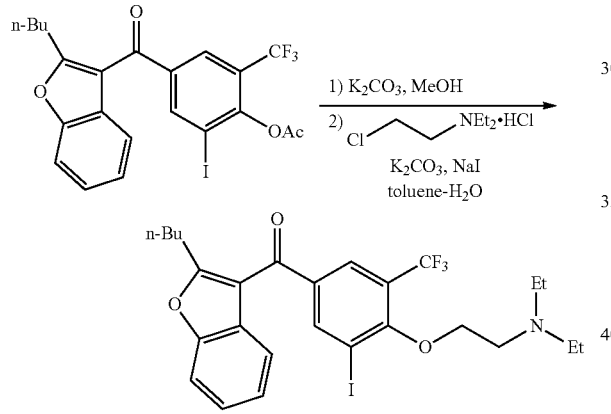

Under air, to 4-(2-butylbenzofuran-3-carbonyl)-2-iodo-6-(trifluoromethyl)phenyl acetate (14 mg, 0.027 mmol, 1.00 equiv), prepared in Example 1, in MeOH (0.5 mL) at 23° C. was added K$_2$CO$_3$ (11 mg, 0.081 mmol, 3.0 equiv). After stirring for 1 h at 23° C., the reaction mixture was concentrated in vacuo and the residue was added 1N HCl (1 mL) and CH$_2$Cl$_2$ (1 mL). The phases were separated and the aqueous phase was extracted with CH$_2$Cl$_2$ (3×1 mL). The combined organic phases were washed with brine (3 mL) and dried (MgSO$_4$). The filtrate was concentrated in vacuo to afford 13 mg of the crude phenol as colorless oil, which was used in the next step without further purification.

Under air, to the crude phenol (<0.027 mmol, 1.0 equiv) in toluene-H$_2$O (0.6 mL-0.3 mL) at 23° C. was added NaI (0.4 mg, 0.003 mmol, 0.1 equiv), K$_2$CO$_3$ (15 mg, 0.11 mmol, 4.0 equiv), and 2-chloro-N,N-diethylethanamine (5.1 mg, 0.030 mmol, 1.1 equiv). After stirring for 2 h at 100° C., the reaction mixture was cooled to 23° C. and CH$_2$Cl$_2$ (0.5 mL) was added. The phases were separated and the aqueous phase was extracted with CH$_2$Cl$_2$ (3×0.5 mL). The combined organic phases were washed with brine (1 mL) and dried (MgSO$_4$). The filtrate was concentrated in vacuo and the residue was purified by preparative TLC eluting with hexanes/EtOAc 1:1 (v/v) to afford 10 mg of the title compound as colorless oil (63% yield, 2 steps). R$_f$=0.40 (hexanes/EtOAc 1:1 (v/v)). $^1$H NMR (300 MHz, CDCl$_3$, 23° C., δ): 8.44 (d, J=1.8 Hz, 1H), 8.07 (d, J=1.8 Hz, 1H), 7.50 (d, J=7.8 Hz, 1H), 7.37 (d, J=7.5 Hz, 1H), 7.32 (dd, J=7.8 Hz, 7.5 Hz, 1H), 7.24 (dd, J=7.8 Hz, 7.5 Hz, 1H), 4.21 (t, J=6.0 Hz, 2H), 3.07 (t, J=6.0 Hz, 2H), 2.86 (t, J=8.1 Hz, 2H), 2.71 (q, J=6.9 Hz, 4H), 1.82-1.72 (m, 2H), 1.41-1.31 (m, 2H), 1.11 (t, J=6.9 Hz, 6H), 0.91 (t, J=7.2 Hz, 3H). $^{19}$F NMR (281 MHz, CDCl$_3$, 23° C., δ): −61.91 (m, 3F).

Example 3

Synthesis of (2-butylbenzofuran-3-yl)(4-(2-(diethylamino)ethoxy)-3-(trifluoromethyl)phenyl)methanone (3)

(2-butylbenzofuran-3-yl)(4-hydroxy-3-(trifluoromethyl)phenyl)methanone

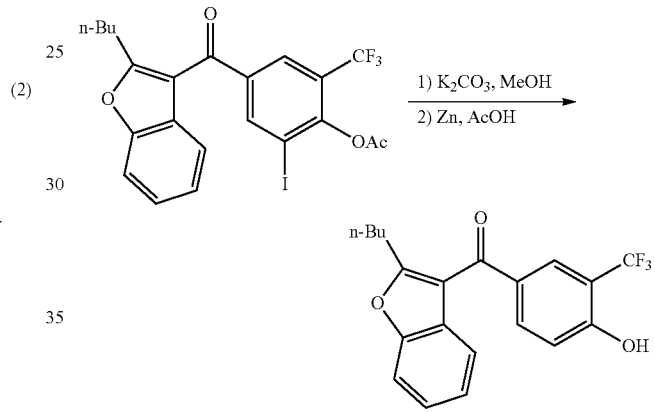

Under air, to 4-(2-butylbenzofuran-3-carbonyl)-2-iodo-6-(trifluoromethyl)phenyl acetate (1.8 g, 3.4 mmol, 1.0 equiv), prepared in Example 1, in MeOH (10 mL) at 23° C. was added K$_2$CO$_3$ (1.4 g, 10 mmol, 3.0 equiv). After stirring for 1.5 h at 23° C., the reaction mixture was concentrated in vacuo and the residue was added 1N HCl (15 mL) and CH$_2$Cl$_2$ (15 mL). The phases were separated and the aqueous phase was extracted with CH$_2$Cl$_2$ (3×10 mL). The combined organic phases were washed with brine (30 mL) and dried (MgSO$_4$). The filtrate was concentrated in vacuo to afford 1.7 g of the crude phenol as colorless oil, which was used in the next step without further purification.

Under air, to the crude phenol (<3.4 mmol, 1.0 equiv) in AcOH (10 mL) at 23° C. was added Zn powder (6.5 g, 10 mmol, 30 equiv). After stirring for 1 hr at 23° C., the reaction mixture was filtered. The filtrate was concentrated in vacuo and the residue was purified by chromatography on silica gel eluting with hexanes/EtOAc to afford 550 mg of the title compound as yellow oil (45% yield, 2 steps). R$_f$=0.75 (hexanes/EtOAc 1:1 (v/v)). NMR Spectroscopy: $^1$H NMR (300 MHz, CDCl$_3$, 23° C., δ): 8.09 (d, J=1.8 Hz, 1H), 7.94 (dd, J=8.7 Hz, 1.8 Hz, 1H), 7.49 (d, J=7.8 Hz, 1H), 7.34 (d, J=7.5 Hz, 1H), 7.26 (dd, J=7.8 Hz, 7.5 Hz, 1H), 7.21 (dd, J=7.8 Hz, 7.5 Hz, 1H), 7.06 (d, J=8.7 Hz, 1H), 2.90 (t, J=8.1 Hz, 2H), 1.83-1.70 (m, 2H), 1.41-1.30 (m, 2H), 0.90 (t, J=7.2 Hz, 3H). $^{19}$F NMR (281 MHz, CDCl$_3$, 23° C., δ): −61.62 (m, 3F).

(2-butylbenzofuran-3-yl)(4-(2-(diethylamino)ethoxy)-3-(trifluoromethyl)phenyl)methanone (3)

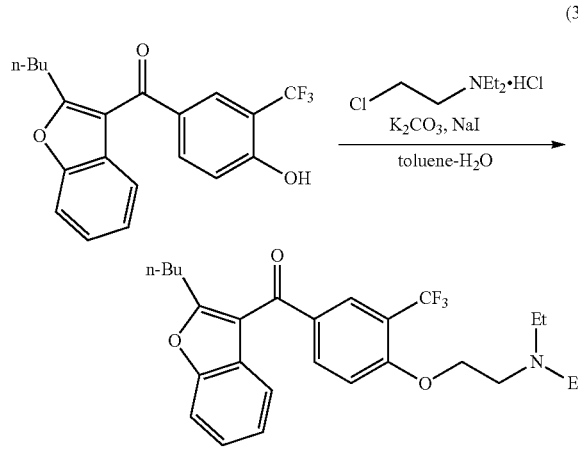

Under air, (2-butylbenzofuran-3-yl)(4-hydroxy-3-(trifluoromethyl)phenyl)methanone (82 mg, 0.23 mmol, 1.0 equiv) in toluene-H$_2$O (1.2 mL-0.6 mL) at 23° C. was added NaI (3.4 mg, 0.023 mmol, 0.1 equiv), K$_2$CO$_3$ (127 mg, 0.92 mmol, 4.0 equiv), and 2-chloro-N,N-diethylethanamine (40 mg, 0.23 mmol, 1.0 equiv). After stirring for 1.5 h at 90° C., the reaction mixture was cooled to 23° C. and CH$_2$Cl$_2$ (1 mL) was added. The phases were separated and the aqueous phase was extracted with CH$_2$Cl$_2$ (3×1 mL). The combined organic phases were washed with brine (3 mL) and dried (MgSO$_4$). The filtrate was concentrated in vacuo and the residue was purified by preparative TLC eluting with hexanes/EtOAc 1:1 to afford 65 mg of the title compound as colorless oil (61% yield). R$_f$=0.35 (hexanes/EtOAc 7:3 (v/v)). NMR Spectroscopy: $^1$H NMR (300 MHz, CDCl$_3$, 23° C., δ): 8.13 (d, J=1.8 Hz, 1H), 8.00 (dd, J=8.7 Hz, 1.8 Hz, 1H), 7.48 (d, J=7.8 Hz, 1H), 7.33 (d, J=7.5 Hz, 1H), 7.29 (dd, J=7.8 Hz, 7.5 Hz, 1H), 7.20 (dd, J=7.8 Hz, 7.5 Hz, 1H), 7.07 (d, J=8.7 Hz, 1H), 4.24 (t, J=6.0 Hz, 2H), 2.97 (t, J=6.0 Hz, 2H), 2.89 (t, J=8.1 Hz, 2H), 2.68 (q, J=6.9 Hz, 4H), 1.82-1.70 (m, 2H), 1.41-1.30 (m, 2H), 1.08 (t, J=6.9 Hz, 6H), 0.90 (t, J=7.2 Hz, 3H). $^{19}$F NMR (281 MHz, CDCl$_3$, 23° C., δ): −62.90 (m, 3F).

Example 4

Synthesis of (2-butylbenzofuran-3-yl)(4-(2-(diethylamino)ethoxy-d$_{14}$)-3-(trifluoromethyl)phenyl)methanone (15)

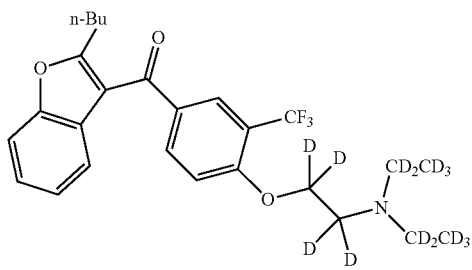

Under air, (2-butylbenzofuran-3-yl)(4-hydroxy-3-(trifluoromethyl)phenyl)methanone (82 mg, 0.23 mmol, 1.0 equiv) in toluene-H$_2$O (1.2 mL-0.6 mL) at 23° C. is added NaI (3.4 mg, 0.023 mmol, 0.1 equiv), K$_2$CO$_3$ (127 mg, 0.92 mmol, 4.0 equiv), and 2-chloro-N,N-diethylethanamine-d$_{14}$ (0.23 mmol, 1.0 equiv). After stirring for 1.5 h at 90° C., the reaction mixture is cooled to 23° C. and CH$_2$Cl$_2$ (1 mL) is added. The phases are separated and the aqueous phase is extracted with CH$_2$Cl$_2$ (3×1 mL). The combined organic phases are washed with brine (3 mL) and dried (MgSO$_4$). The filtrate is concentrated in vacuo and the residue is purified by preparative TLC eluting with hexanes/EtOAc 1:1 to afford the title compound 15.

Example 5

Testing for Cardiac Ion Channel Activity

Compounds of the present invention were tested for their anti-arrhythmic activity in a series of in vitro cardiac ion channel assays using cloned human channels expressed in CHO cells or HEK293 cells:

1. Cloned L-type calcium channels (hCav1.2, encoded by the human CACNA1C gene and coexpressed with the β2 subunit, encoded by the human CACNB2 gene and the α2δ1 subunit encoded by the human CACNA2D1 gene, in CHO cells), responsible for I$_{Ca,L}$, high threshold calcium current.
2. Cloned hERG potassium channels (encoded by the KCNH2 gene and expressed in human embryonic kidney, HEK293, cells) responsible for I$_{Kr}$.
3. Cloned hKir2.1 potassium channels (encoded by the human KCNJ2 gene and expressed in HEK293 cells), responsible for I$_{K1}$, inwardly rectifying potassium current.
4. Cloned hKvLQT1/hminK potassium channels (encoded by the human KCNQ1 and KCNE1 genes and coexpressed in CHO cells), responsible for I$_{Ks}$, slow delayed rectifier potassium current.
5. Cloned hKv1.5 potassium channels (encoded by the human KCNA5 gene and expressed in CHO cells), responsible for I$_{Kur}$, ultra-rapid delayed rectifier potassium current.
6. Cloned hNav1.5 sodium channels (SCN5A gene, expressed in CHO cells).
7. Cloned hKir3.1/hKir3.4 potassium channels (expressed by the human KCNJ3 and KCNJ5 genes and co-expressed in HEK293 cells) responsible for I$_{ACh}$, inwardly rectifying potassium current.

One concentration of a compound of the present invention was applied for a five-minute interval via disposable polyethylene micropipette tips to naïve cells (n≥2, where n=the number cells/concentration). Each solution exchange, performed in quadruplicate, consisted of aspiration and replacement of 45 µL volume of the extracellular well of the Sealchip$_{16}$. Duration of exposure to the test compound was three minutes. For the hKir3.1/hKir3.4 assay, two concentrations of a compound of the present invention were used and the duration of exposure was 3 minutes.

In preparation for an automated patch clamp procedure recording session, intracellular solution was loaded into the intracellular compartments of the Sealchip$_{16}$ or Qplate planar electrode. Cell suspension was pipetted into the extracellular compartments of the Sealchip$_{16}$ or Qplate planar electrode. After establishment of a whole-cell configuration, membrane currents were recorded using dual-channel patch clamp amplifiers in the PatchXpress® or Qpatch HT® system. Before digitization, the current records were low-pass filtered at one-fifth of the sampling frequency.

Valid whole-call recordings met the following criteria:
1. Membrane resistance (Rm)≥200 MΩ
2. Leak current≤25% channel current.

hCav1.2 Test Procedure

Onset and steady state block of hCav1.2/β2/α2δ channels were measured using a stimulus voltage pattern consisting of a depolarizing test pulse (duration, 200 ms; amplitude, 10 mV) at 10 intervals from a −80 mV holding potential. Peak current was measured during the step to 10 mV. Saturating concentration of positive control, nifedipine (10 μM), was added at the end of each experiment to block hCav1.2 current. Leakage current was digitally subtracted from the total membrane current record.

hERG Test Procedure

Onset and block of hERG current was measured using a stimulus voltage pattern consisting of a 500 ms prepulse to −40 mV (leakage subtraction), a 2-second activating pulse to +40 mV, followed by a 2-second test pulse to −40 mV. Leakage current was calculated from the current amplitude evoked by the prepulse and subtracted from the total membrane current record.

hKir2.1 Test Procedures

Onset and steady state block of hKir2.1 current was measured using a pulse pattern with fixed amplitudes (hyperpolarization: −110 mV amplitude, 300 ms duration) repeated at 10 s intervals from a holding potential of −70 mV. Current amplitude was measured at the end of the step to −110 mV.

hKvLQT1/hminK Test Procedures

Onset and steady state block of hKvLQT1/hminK current was measured using a pulse pattern with fixed amplitudes (depolarization: +40 mV for 2 s; repolarization: −40 mV for 0.5 s) repeated at 15 s intervals from a holding potential of −80 mV. Current amplitude was measured at the end of the step to +40 mV. Saturating concentration of positive control, chromanol 293B (300 μM), was added at the end of each experiment to block hKvLQT1/hminK current. Leakage current was measured after chromanol 293B addition and subtracted from the total membrane current record.

hKv1.5 Test Procedure

Onset and steady state block of hKv1.5 current was measured using a pulse pattern with fixed amplitudes (depolarization: +20 mV amplitude, 300 ms duration) repeated at 10 s intervals from a holding potential of −80 mV. Current amplitude was measured at the end of the step to +20 mV.

hNav1.5 Test Procedure

Onset and steady-state block of hNav1.5 current was measured using double pulse pattern consisting of a series of two depolarizing test pulses to −15 mV. From a holding potential of −80 mV, an initial hyperpolarizing conditioning pre-pulse (−120 mV amplitude, 200 ms duration,) was followed immediately by the first depolarizing test pulse to −15 mV (200 ms duration). This was followed by a hyperpolarizing conditioning inter-pulse to −80 mV (200 ms duration) and then a second depolarizing test pulse to −15 mV for 20 ms. The pulse pattern was repeated at 10 s intervals and peak current amplitudes at both test pulses were measured.

hKir3.1/hKir3.4 Test Procedure

The in vitro effects of the compounds of the present invention were evaluated at room temperature using the PatchXpress (Model 7000A, Molecular Devices, Union City, Calif.), an automated parallel patch clamp system.

Table 3 shows the cardiac ion channel inhibition data for compounds synthesized in Examples 1, 2, and 3.

TABLE 3

| Ion Channel @10 μM | Amiodarone | Compound 1 | Compound 2 | Compound 3 |
|---|---|---|---|---|
| Nav1.5 tonic | 6.8% | 11.5% | 23% | 48% |
| Nav1.5 phasic | 44% | 26% | 44% | 86% |
| Cav1.2 | 7.7% | 101% | 81% | 2% |
| hERG | 65% | 55% | 75% | 74% |
| Kv1.5 | 0.7% | 54% | 21% | 25% |
| Kir2.1 | 0.9% | 0.3% | 2.7% | 9.7% |
| KvLQT | −0.6% | 49% | 2.5% | 8.4% |
| K(ach) | 23% | 49% | 4.6% | 11% |
| K(ach) @1 μM | 4.5% | 16% | 1.4% | 2.1% |

What is claimed:
1. A compound of formula II:

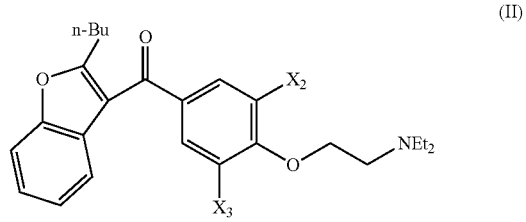

or a pharmaceutically acceptable salt or solvate thereof, wherein $X_2$ is $CF_3$ and $X_3$ is selected from hydrogen, I, F, $CF_3$, $CHF_2$, $CH_2F$, $OCF_3$, $OCHF_2$, and $OCH_2F$.

2. The compound of claim 1, wherein $X_3$ is selected from hydrogen, I, F, $CF_3$, $CHF_2$, and $CH_2F$.

3. The compound of claim 1, wherein $X_3$ is selected from hydrogen, I, and $CF_3$.

4. A compound of formula II:

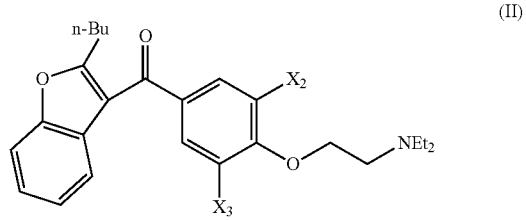

or a pharmaceutically acceptable salt or solvate thereof, wherein $X_3$ is hydrogen and $X_2$ is selected from F, $CF_3$, $CHF_2$, $CH_2F$, $OCF_3$, $OCHF_2$, and $OCH_2F$.

5. The compound of claim 4, wherein $X_2$ is selected from F, $CF_3$, $CHF_2$, and $CH_2F$.

6. The compound of claim 1 of formula VII:

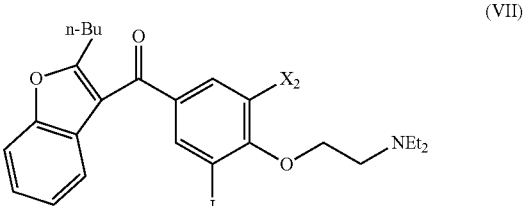

or a pharmaceutically acceptable salt thereof.

7. A compound selected from

| Compound # | |
|---|---|
| 1 | 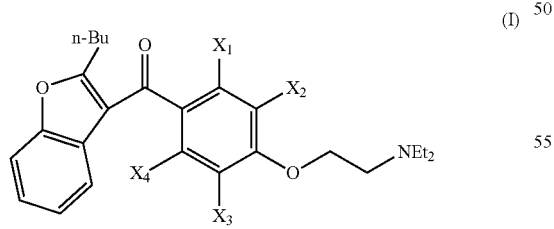 |
| 2 | |
| 3 | |
| 11 | | or a pharmaceutically acceptable salt or solvate thereof.

8. A pharmaceutical composition comprising at least one compound of claim 1 or a pharmaceutically acceptable salt or solvate thereof and one or more pharmaceutically acceptable carrier or excipient.

9. A compound of formula I:

(I)

or a pharmaceutically acceptable salt or solvate thereof, wherein $X_1$, $X_2$, $X_3$, and $X_4$ are each independently selected from hydrogen, I, F, $CF_3$, $CHF_2$, $CH_2F$, $OCF_3$, $OCHF_2$, and $OCH_2F$, provided that at least one of $X_1$, $X_2$, $X_3$, and $X_4$ is F or a group of atoms containing at least one fluorine atom; and wherein at least one hydrogen in the compound is substituted with a deuterium.

10. A deuterium labeled The compound of claim 9 that is

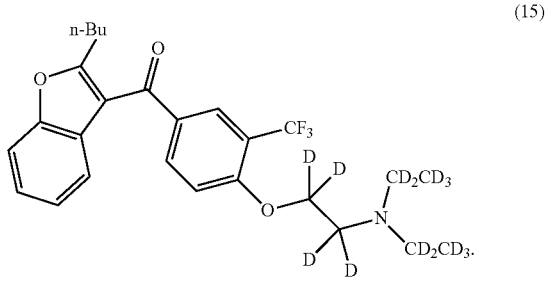

(15)

11. The compound of claim 7, wherein the compound is

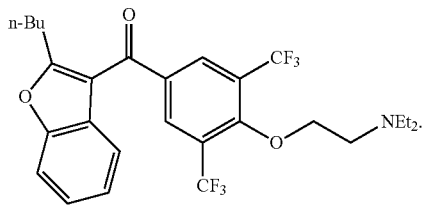

12. The compound of claim 7, wherein the compound is

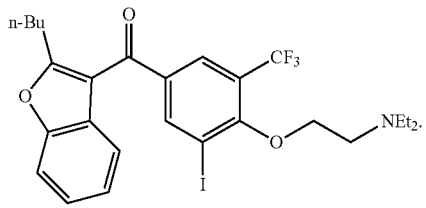

13. The compound of claim 7, wherein the compound is

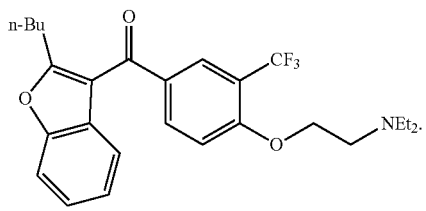

14. The compound of claim 7, wherein the compound is

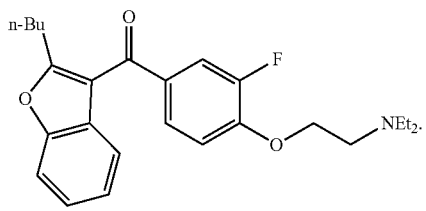

15. A pharmaceutical composition comprising at least one compound of claim 4 or a pharmaceutically acceptable salt or solvate thereof and one or more pharmaceutically acceptable carrier or excipient.

16. A pharmaceutical composition comprising at least one compound of claim 7 or a pharmaceutically acceptable salt or solvate thereof and one or more pharmaceutically acceptable carrier or excipient.

* * * * *

UNITED STATES PATENT AND TRADEMARK OFFICE
CERTIFICATE OF CORRECTION

| | | |
|---|---|---|
| PATENT NO. | : 9,624,189 B2 | Page 1 of 1 |
| APPLICATION NO. | : 13/796248 | |
| DATED | : April 18, 2017 | |
| INVENTOR(S) | : Mark E. Duggan et al. | |

It is certified that error appears in the above-identified patent and that said Letters Patent is hereby corrected as shown below:

In the Claims

Claim 10, at Column 28, Line number 1:
"10. A deuterium labeled The compound of claim 9 that is"

Should read:
-- 10. The compound of claim 9 that is --

Signed and Sealed this
Sixth Day of June, 2017

Michelle K. Lee
*Director of the United States Patent and Trademark Office*